(12) United States Patent
Breidenbach

(10) Patent No.: US 10,578,519 B2
(45) Date of Patent: Mar. 3, 2020

(54) WELDLESS BAILER

(71) Applicant: Aqua Bailers, Inc., Knoxville, TN (US)

(72) Inventor: Michael A. Breidenbach, Knoxville, TN (US)

(73) Assignee: Aqua Bailers, Inc., Knoxville, TN (US)

(*) Notice: Subject to any disclaimer, the term of this patent is extended or adjusted under 35 U.S.C. 154(b) by 273 days.

(21) Appl. No.: 15/702,350

(22) Filed: Sep. 12, 2017

(65) Prior Publication Data

US 2019/0078983 A1 Mar. 14, 2019

(51) Int. Cl.
*G01N 1/12* (2006.01)
*G01D 11/24* (2006.01)

(52) U.S. Cl.
CPC ............... *G01N 1/12* (2013.01); *G01D 11/24* (2013.01)

(58) Field of Classification Search
CPC ............. G01N 1/10; G01N 1/12; G01D 11/24
USPC ................... 73/864, 864.51, 864.63, 864.91
See application file for complete search history.

(56) References Cited

U.S. PATENT DOCUMENTS

| 4,590,810 | A | * | 5/1986 | Hunkin | G01N 1/12 73/863.71 |
| 5,404,949 | A | | 4/1995 | Voss | |
| 5,597,966 | A | * | 1/1997 | Timmons | E21B 27/005 73/863.72 |
| 5,878,813 | A | | 3/1999 | Ridgeway, Jr. | |
| 6,457,760 | B1 | * | 10/2002 | Pratt | E21B 27/00 137/533.21 |
| 7,028,564 | B2 | | 4/2006 | Voss | |
| 2002/0185878 | A1 | * | 12/2002 | Pratt | G01N 1/12 294/68.25 |

* cited by examiner

*Primary Examiner* — Benjamin R Schmitt
(74) *Attorney, Agent, or Firm* — Pitts & Lake, P.C.

(57) ABSTRACT

A liquid sampling device including a cylindrical body having a first plurality of grooves formed with irregular spacing near a first end of the cylindrical body, and a second plurality of grooves formed with irregular spacing near a second end of the cylindrical body, a top cap having an insertion portion to fit inside the cylindrical body and having a plurality of ridges formed thereon to correspond to the first plurality of grooves, and a cap portion having a suspension member, and a bottom cap having an insertion portion to fit inside the cylindrical body and having a plurality of ridges formed thereon to correspond to the second plurality of grooves, and an external annular flange forming an opening in the bottom cap to pass liquid therethrough, wherein the ridges of the top and bottom caps are configured to form snap fits with the corresponding grooves of the cylindrical body.

15 Claims, 6 Drawing Sheets

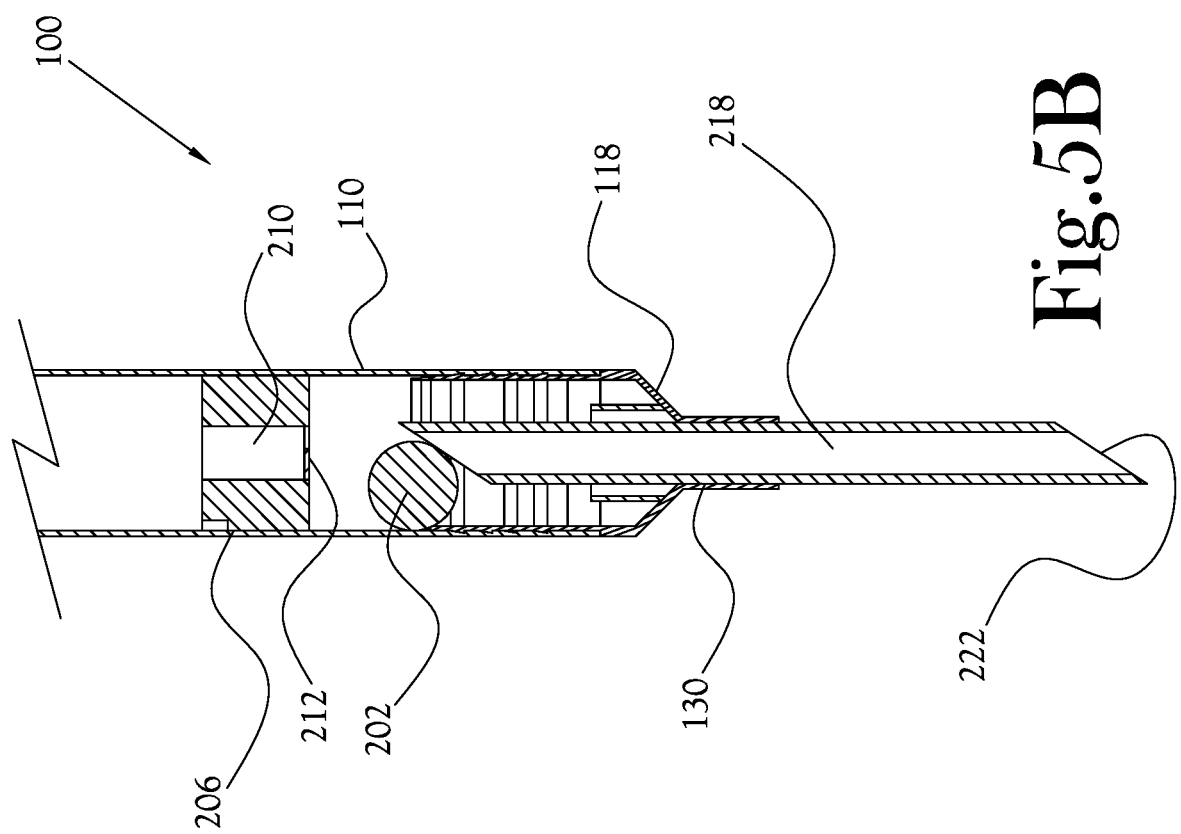
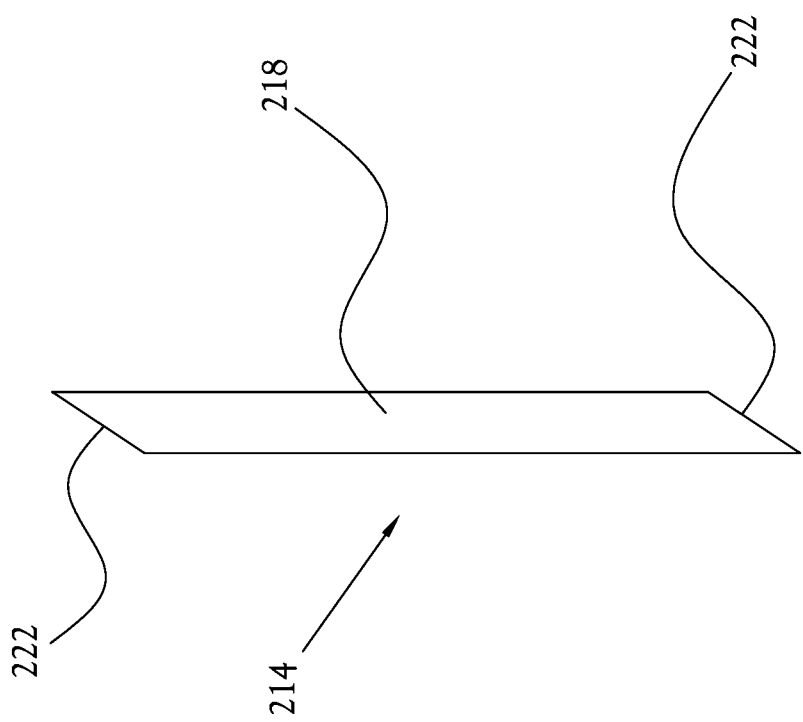
Fig.5B
Fig.5A

WELDLESS BAILER

CROSS-REFERENCE TO RELATED APPLICATIONS

Not applicable.

FIELD OF INVENTION

The present general inventive concept relates to a bailer for collecting liquid samples, and, more particularly, to a weldless bailer having a snap fit assembly to increase convenience of production and use.

BACKGROUND

Testing for groundwater pollution is routine and necessary around many types of industrial and commercial facilities in which waste, spilled chemicals, and the like may contaminate nearby groundwater. Such testing typically includes employing monitoring wells and collecting water from these monitoring wells to test for contaminants. While there are many devices that may be used for such collecting of water from the monitoring wells, bailers are a preferred way to gather these samples. Bailers are elongated, hollow structures that typically have a one-way valve at the bottom for water to enter into. A typical bailer is attached to a rope or cord at a top end, and is lowered into the monitoring well to allow the liquid in the monitoring well to enter into the bailer through the one-way valve, and then simply lifted up out of the well. Such bailers are in wide use because they require no internal power and are inexpensive to fabricate and use. However, because the internal workings of the bailers typically require some moving parts, the bailers must be assembled from pre-fabricated pieces, and typically have at least capping bodies at either end of the bailer. Since conventional bailers are typically constructed of a plastic polymer, these end parts are typically welded to the body of the bailer. However, the welding of these components are problematic, at least in that spot welding produces too weak a bond which may come apart in use, and ultrasonic welding, which produces a stronger bond, is prohibitively expensive. This is especially problematic when dissimilar plastics are used in the fabrication of the bailer, because very good bonds are needed when welding different polymers. Therefore, there exists a need for a bailer that may be fabricated and assembled without problems such as these.

BRIEF SUMMARY

According to various example embodiments of the present general inventive concept, a weldless bailer is provided that includes end caps that form snap fits with the body of the bailer such that welding is not required. In various example embodiments, a weighted member is provided in the bailer to provide anti-buoyancy to the bailer and to limit the travel of a ball valve located therein.

Additional aspects and advantages of the present general inventive concept will be set forth in part in the description which follows, and, in part, will be obvious from the description, or may be learned by practice of the present general inventive concept.

The foregoing and/or other aspects and advantages of the present general inventive concept may be achieved by providing a liquid sampling device including a substantially cylindrical body configured to have a first plurality of grooves formed concentrically and with irregular spacing proximate a first end of the cylindrical body, and a second plurality of grooves formed concentrically and with irregular spacing proximate a second end of the cylindrical body, a top cap having a substantially cylindrical insertion portion configured to fit inside the cylindrical body and to have a plurality of ridges formed concentrically thereon so as to correspond to the first plurality of grooves, and a cap portion formed with a suspension member configured to receive a suspension element from which the liquid sampling device may hang, and a bottom cap having a substantially cylindrical insertion portion configured to fit inside the cylindrical body and to have a plurality of ridges formed concentrically thereon so as to correspond to the second plurality of grooves, and a cap portion including an external annular flange forming an opening in the bottom cap to pass liquid therethrough into the liquid sampling device, wherein the ridges of the top and bottom caps are configured to form snap fits with the corresponding grooves of the cylindrical body.

The foregoing and/or other aspects and advantages of the present general inventive concept may also be achieved by providing a liquid sampling device including a substantially cylindrical body having first and second ends, a top cap configured to cap a first end of the cylindrical body and formed with a suspension member configured to receive a suspension element from which the liquid sampling device may hang, a bottom cap configured to cap a second end of the cylindrical body and formed with an external annular flange forming an opening in the bottom cap and sharing an axis with the cylindrical body; a ball valve configured to have a diameter larger than the external annular flange such that the ball valve may close the opening in the bottom cap formed by the external annular flange, and a weighted insert configured to fit snuggly inside the cylindrical body at a predetermined position to provide anti-buoyancy to the liquid sampling device and to limit upward movement of the ball valve while allowing liquid to pass therethrough.

The foregoing and/or other aspects and advantages of the present general inventive concept may also be achieved by providing a liquid sampling device including a substantially cylindrical body configured to have a first plurality of grooves formed concentrically and with irregular spacing on an inner surface proximate a first end of the cylindrical body, and a second plurality of grooves formed concentrically and with irregular spacing on an inner surface proximate a second end of the cylindrical body, a top cap having a substantially cylindrical insertion portion configured to fit snugly inside the cylindrical body and to have a plurality of step down portions at a distal end thereof, the insertion portion of the top cap configured to have a plurality of ridges formed concentrically thereon so as to correspond to the first plurality of grooves, and a cap portion configured to abut against the first end of the cylindrical body and to have a tapered portion with an opening formed to pass therethrough such that two symmetrical orifices are formed in the tapered portion, a bottom cap having a substantially cylindrical insertion portion configured to fit snugly inside the cylindrical body and to have a plurality of step down portions at a distal end thereof, the insertion portion of the bottom cap configured to have a plurality of ridges formed concentrically thereon so as to correspond to the second plurality of grooves, and a cap portion configured to abut against the second end of the cylindrical body, to have a tapered portion terminating at an external annular flange forming an opening in the bottom cap, and to have an internal annular flange extending inwardly from the tapered portion and having a larger diameter than the external annular flange, a ball valve configured to have a diameter larger than the external annular flange and smaller than the internal annular flange such that the ball valve may close the opening in the bottom cap formed by the external annular flange, and a weighted insert configured to fit snuggly inside the cylindrical body at a predetermined position to provide anti-buoyancy to the liquid sampling device and to limit upward movement of the ball valve, the weighted insert having a central channel configured to allow liquid therethrough and a grating provided at a bottom of the central channel configured to prevent the ball valve from blocking the central channel, wherein the top and bottom caps are hollow to form pathways from inside the cylindrical body to outside of the top and bottom caps, and wherein the ridges of the top and bottom caps are configured to form snap fits with the corresponding grooves of the cylindrical body.

Other features and aspects may be apparent from the following detailed description, the drawings, and the claims.

BRIEF DESCRIPTION OF THE FIGURES

The following example embodiments are representative of example techniques and structures designed to carry out the objects of the present general inventive concept, but the present general inventive concept is not limited to these example embodiments. In the accompanying drawings and illustrations, the sizes and relative sizes, shapes, and qualities of lines, entities, and regions may be exaggerated for clarity. A wide variety of additional embodiments will be more readily understood and appreciated through the following detailed description of the example embodiments, with reference to the accompanying drawings in which:

FIGS. 5A-B illustrate a drainage member for the liquid sampling device according to an example embodiment of the present general inventive concept.

DETAILED DESCRIPTION

Figure 1:
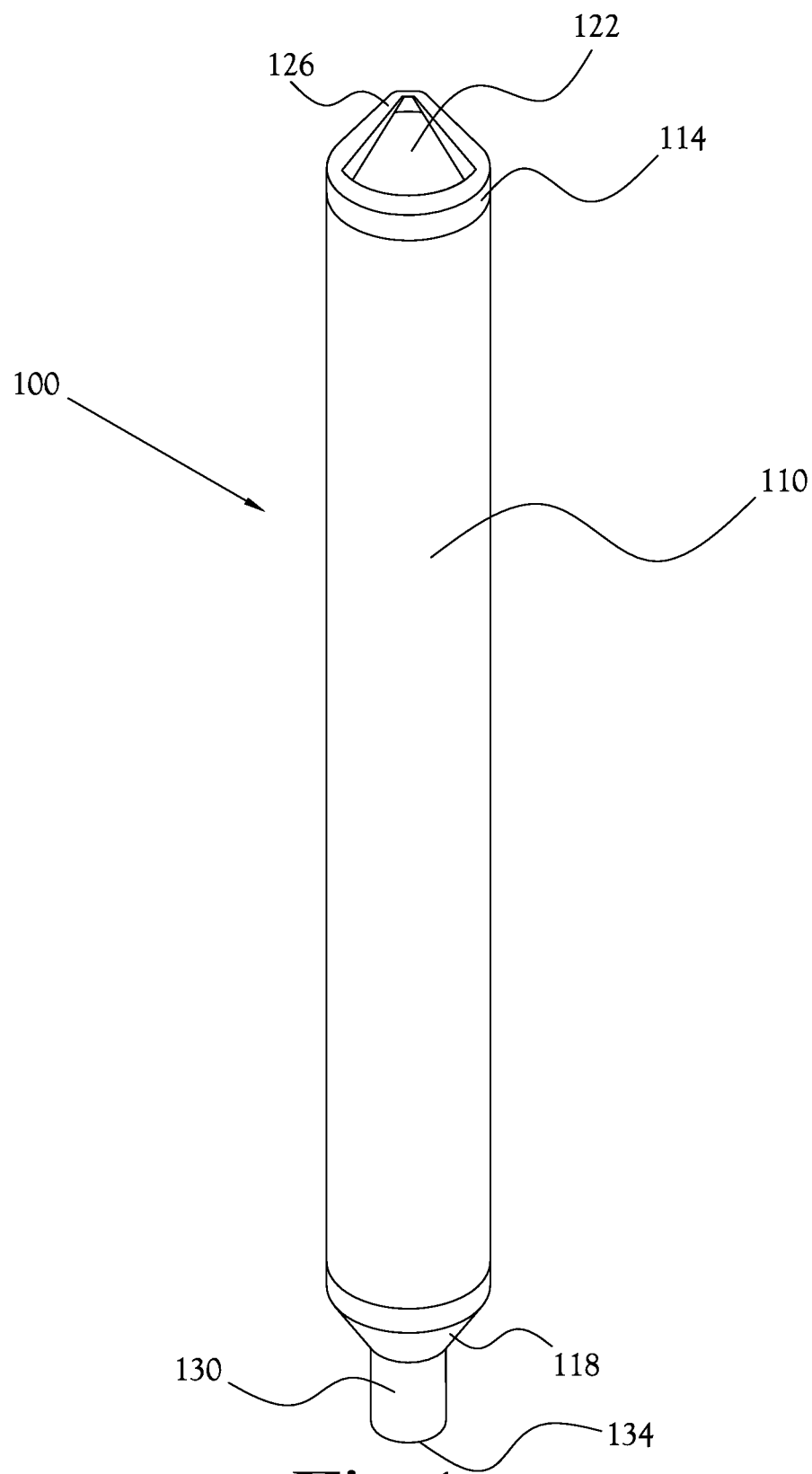
FIG. 1 illustrates a liquid sampling device according to an example embodiment of the present general inventive concept.

Reference will now be made to the example embodiments of the present general inventive concept, examples of which are illustrated in the accompanying drawings and illustrations. The example embodiments are described herein in order to explain the present general inventive concept by referring to the figures.

The following detailed description is provided to assist the reader in gaining a comprehensive understanding of the structures and fabrication techniques described herein. Accordingly, various changes, modification, and equivalents of the structures and fabrication techniques described herein will be suggested to those of ordinary skill in the art. The progression of fabrication operations described are merely examples, however, and the sequence type of operations is not limited to that set forth herein and may be changed as is known in the art, with the exception of operations necessarily occurring in a certain order. Also, description of well-known functions and constructions may be simplified and/or omitted for increased clarity and conciseness.

Note that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. Spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

According to various example embodiments of the present general inventive concept, a weldless bailer is provided that includes end caps that form snap fits with the body of the bailer such that welding is not required. Such a bailer, or liquid sampling device, may include a cylindrical body having a first plurality of grooves formed with irregular spacing near a first end of the cylindrical body, and a second plurality of grooves formed with irregular spacing near a second end of the cylindrical body, a top cap having an insertion portion to fit inside the cylindrical body and having a plurality of ridges formed thereon to correspond to the first plurality of grooves, and a cap portion having a suspension member, and a bottom cap having an insertion portion to fit inside the cylindrical body and having a plurality of ridges formed thereon to correspond to the second plurality of grooves, and an external annular flange forming an opening in the bottom cap to pass liquid therethrough, wherein the ridges of the top and bottom caps are configured to form snap fits with the corresponding grooves of the cylindrical body. In various example embodiments, a weighted member is provided in the bailer to provide anti-buoyancy to the bailer and to limit the travel of a ball valve located therein.

FIG. 1 illustrates a liquid sampling device according to an example embodiment of the present general inventive concept. The example embodiment liquid sampling device 100 of FIG. 1 includes a hollow and substantially cylindrical body 110 into which a liquid sample may be passed and stored, a top cap 114 provided at a top end of the cylindrical body 110, and a bottom cap 118 provided at a bottom end of the cylindrical body. The top cap 114 shares an axis with the cylindrical body 110, and is formed with an throughway or attachment orifice 122 passing therethrough so as to form symmetrical openings in the top cap 114 under a suspension portion 126 formed over the attachment orifice 122. This symmetry allows the liquid sampling device 100 to be suspended by the suspension portion 126 and maintain a substantially vertical orientation when being lowered into, or lifted out of, wells from which the liquid to be tested is drawn. For example, the bailer 100 may be suspended from a cord or hook that is threaded through the attachment orifice to interact with the suspension portion 126, and since the crook of the suspension portion 126 is centered on an axis of the bailer 100, the bailer may be maintained in a substantially vertical orientation throughout being lowered into, and lifted out of, the monitoring well. The bottom cap 118 is provided with an external annular flange 130 having an intake orifice 134 formed therethrough and through which liquid enters and exits the cylindrical body 110. The external annular flange 130 shares an axis with the cylindrical body 110. The top cap 114 and bottom cap 118 are at least partially tapered to aid in preventing snags with obstructions that may be encountered when lowering/raising the liquid sampling device 100 into/from testing wells.

Figure 2A:
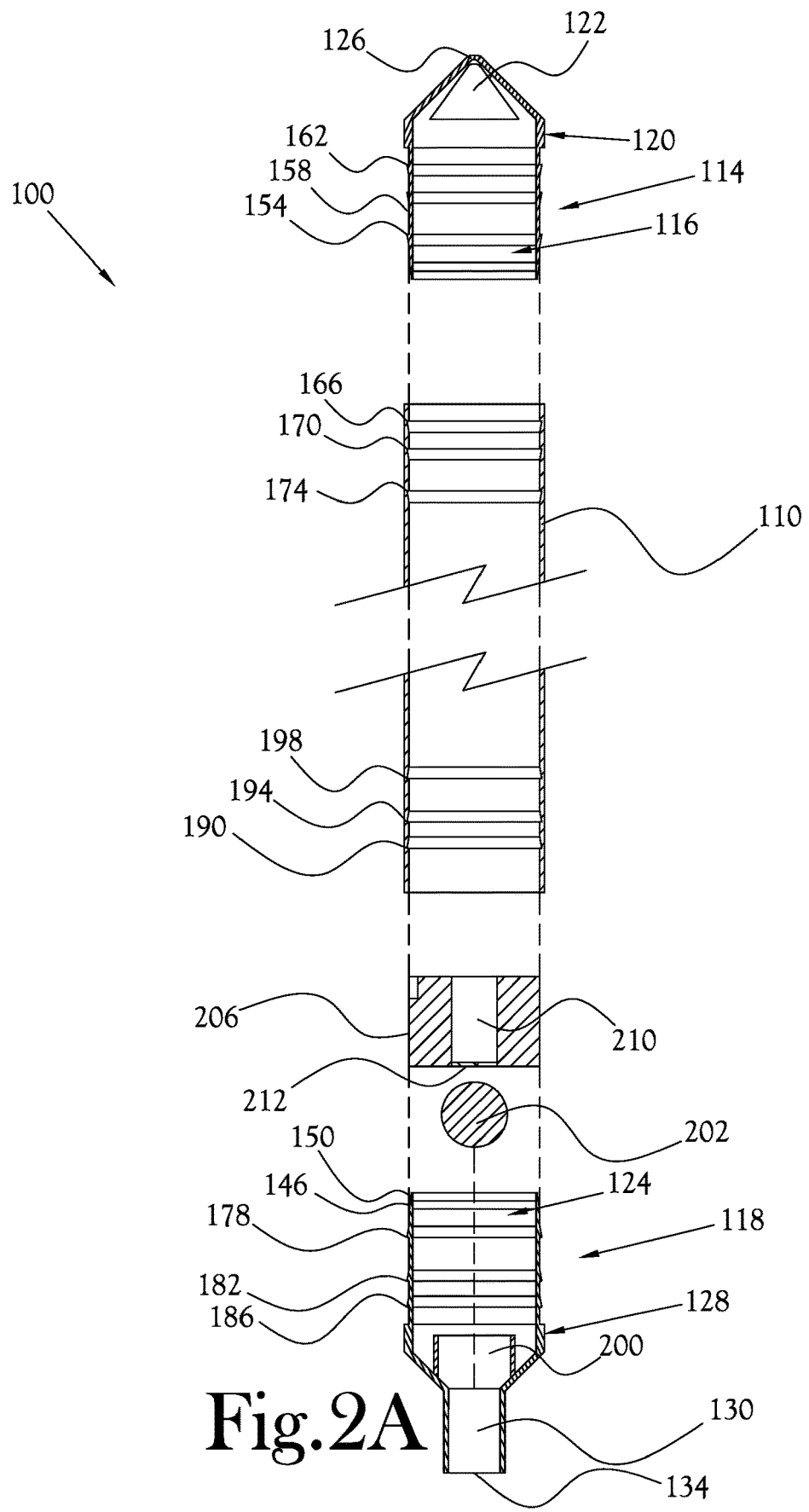
FIG. 2A illustrates an exploded cross section of the embodiment illustrated in FIG. 1.
Figure 2B:
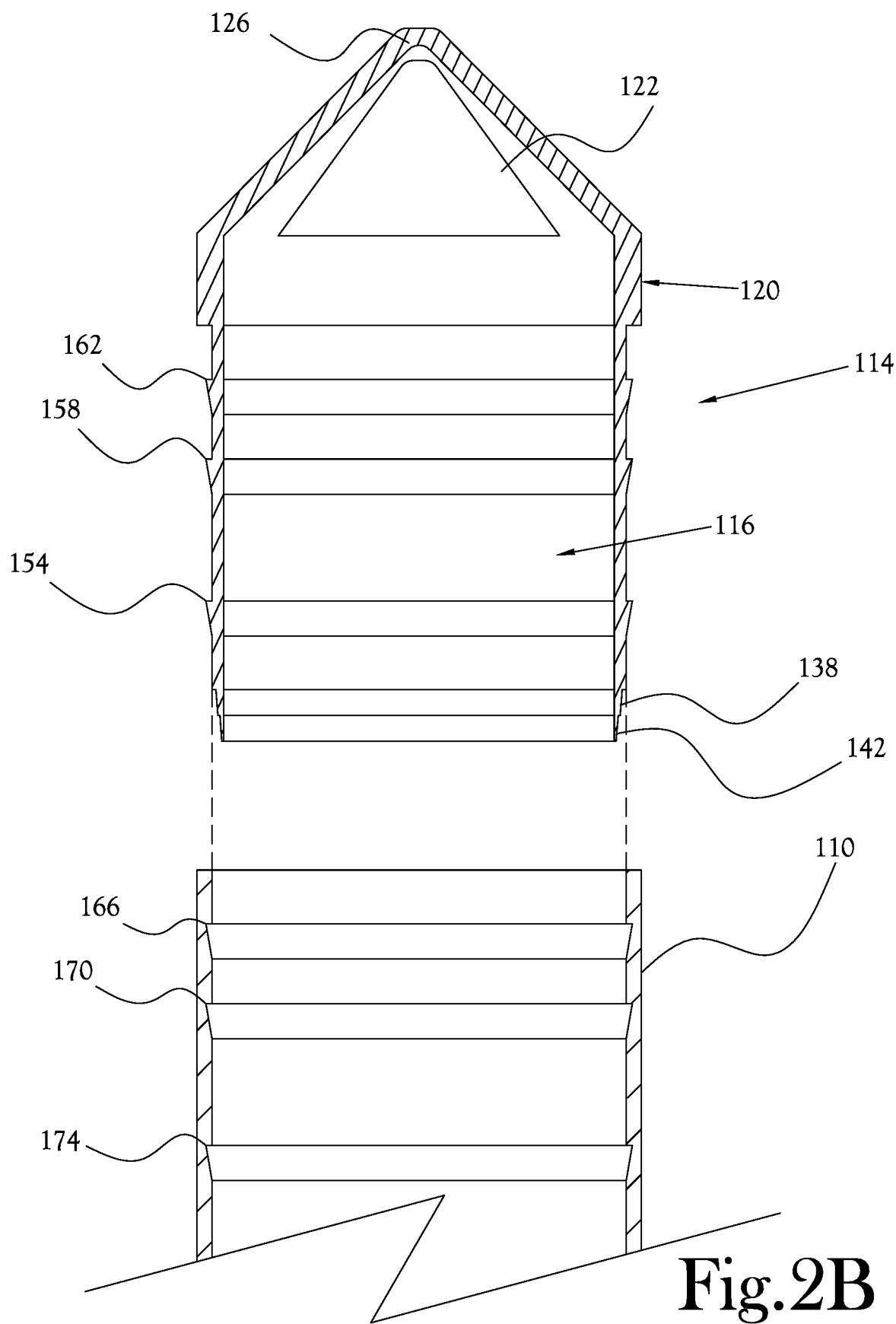
FIG. 2B illustrates a blown-up view of the upper portion of FIG. 2A.

FIG. 2A illustrates an exploded cross section of the embodiment illustrated in FIG. 1, and FIG. 2B illustrates a blown-up view of the upper portion of FIG. 2A. It is understood that various example embodiments of the present general inventive concept may include more or fewer components, and in different configurations, than those illustrated in this example embodiment. In the example embodiment illustrated in FIGS. 2A-2B, the top cap 114 includes an insertion portion 116 that has a slightly smaller diameter than a capping portion 120 of the top cap 114, so that the insertion portion 116 may fit into a top end of the cylindrical body of the liquid sampling device 100. A series of ridges 154,158,162 are formed along the outer perimeter of the insertion portion 116 of the top cap 114, and are spaced to correspond to a series of grooves 166,170,174 that are formed on an inner perimeter proximate a top end of the cylindrical body 110. When the insertion portion 116 of the top cap 114 is moved into the top end of the cylindrical body 110 of the example embodiment illustrated in FIGS. 2A-2B, the ridges 154,158,162 will form a snap fit with the grooves 166,170,174. In this example embodiment, the ridges 154, 158,162 are formed with angled sides on the side that will be slid into the cylindrical body, and the other sides of the ridges are substantially flat. The grooves 166,170,174 are formed to substantially register to the ridges 154,158,162 such that when the top cap 114 is slid into place in the cylindrical body 110, the shapes of the grooves 166,170,174 register with corresponding ridges 154,158,162 to form snap fits. Thus, when the insertion portion 116 of the top cap 114 is slid all the way into the top end of the cylindrical body 110 until the capping portion 120 abuts the end of the cylindrical body 110, the flat portion of the lowest upper ridge 154 abuts the flat portion of the lowest upper groove 174, the flat portion of the middle upper ridge 158 abuts the flat portion of the middle upper groove 170, and the flat portion of the highest upper ridge 162 abuts the flat portion of the highest upper groove 166 to form a snap fit which prevents the top cap 114 from being removed from the cylindrical body 110. As the ridges and grooves are formed to register to one another, the angle portions also respectively face one another in this snap fit arrangement. In the example embodiment illustrated in FIGS. 2A-2B, the cylindrical body 110 is formed of polyvinyl chloride (PVC), and the top and bottom caps 114,118 are formed of polyethylene. Since polyethylene is more flexible than PVC, the insertion portion 116 is malleable enough so that the ramped portions of the ridges 154,158,162 can be slid into the inner circumference of the cylindrical body and then expand into the corresponding grooves 166,170,174 to form the snap fit and allow the remaining outer circumference of the insertion portion 116 to be snugly fit with the remaining inner circumference of the cylindrical body 110. Other embodiments may be provided in which the cylindrical body 110 and the top and bottom caps 114, 118 are formed of other materials, such as for example polyvinyl chloride (PVC), various polyethylene materials, such as for example high density polyethylene (HDPE), polypropylene, or other suitably rigid polymer materials or other materials, and such other materials may be used without departing from the spirit and scope of the present general inventive concept.

In the example embodiment illustrated in FIGS. 2A-2B, the ridges 154,158,162 and corresponding grooves 166,170, 174 are irregularly spaced apart. Such an arrangement aids in the assembly of the liquid sampling device 100 because as the insertion portion 116 of the top cap 114 is being slid into the end of the cylindrical body, the lowest upper ridge 154 will first connect, register, fit, etc., with the highest upper groove 166. The snap fit formed in that connection will be audible. However, the insertion portion 116 needs to be slid further into the cylindrical body 110 so that all of the ridges form the snap fit with all of the corresponding grooves. The angled sides of the ridges and grooves aid in sliding past the initial single snap fits. The irregular spacing of the ridges and grooves is configured such that no more than one ridge will snap into place in one groove at any one time until all three upper ridges 154,158,162, simultaneously snap into all three corresponding upper grooves 166, 170,174. When all three snap fits are simultaneously made, the audible "click" will be much louder than the "click" sounded when only one connection is made. Therefore, an assembler has a readily recognized audio indicator that the full connection has been made. The snap fit provided by the three illustrated ridges and grooves is strong, and formed such that the tensile strength of the top cap 114, such as at the suspension portion 126, will fail before the snap fits could be overcome to separate the top cap 114 from the cylindrical body 110. A portion of FIG. 2A has been blown-up on FIG. 2B to better show the various structures of the top cap 114 and top end of the cylindrical body 110.

The top cap 114 of the embodiment illustrated in FIGS. 2A-2B is also formed with two stepped down portions at a distal end of the insertion portion 116. The first stepped portion 138 decreases the outer diameter of the insertion portion 116, and the second stepped portion 142 further decreases the outer diameter of the insertion portion 116, to make it easier to guide the insertion portion 116 into the top end of the cylindrical body 110 during the assembly process.

The bottom cap 118 is configured with the same snap fit components as those provided to the top cap 114, and forms the same snap fits with the bottom end of the cylindrical body 110. As illustrated in FIG. 2A, the bottom cap 118 includes an insertion portion 124 and capping portion 128, a first stepped portion 146 and second stepped portion 150, and ridges 178,182,186 formed to register with corresponding grooves 190,194,198 formed in the lower end of the cylindrical body 110. The ridges and grooves used to attach the bottom cap 118 to the bottom end of the cylindrical body 110 have the same irregular spacing as that provided to the top assembly. While having the same configuration of irregular spacing of ridges and grooves at either end of the liquid sampling device 100 may reduce fabrication time and costs, other various example embodiments of the present general inventive concept may provide different ridge and groove orientations at either or both ends of the bailer 100. Similarly, other various example embodiments may provide different numbers of registered ridge and groove pairings.

Figure 4A:
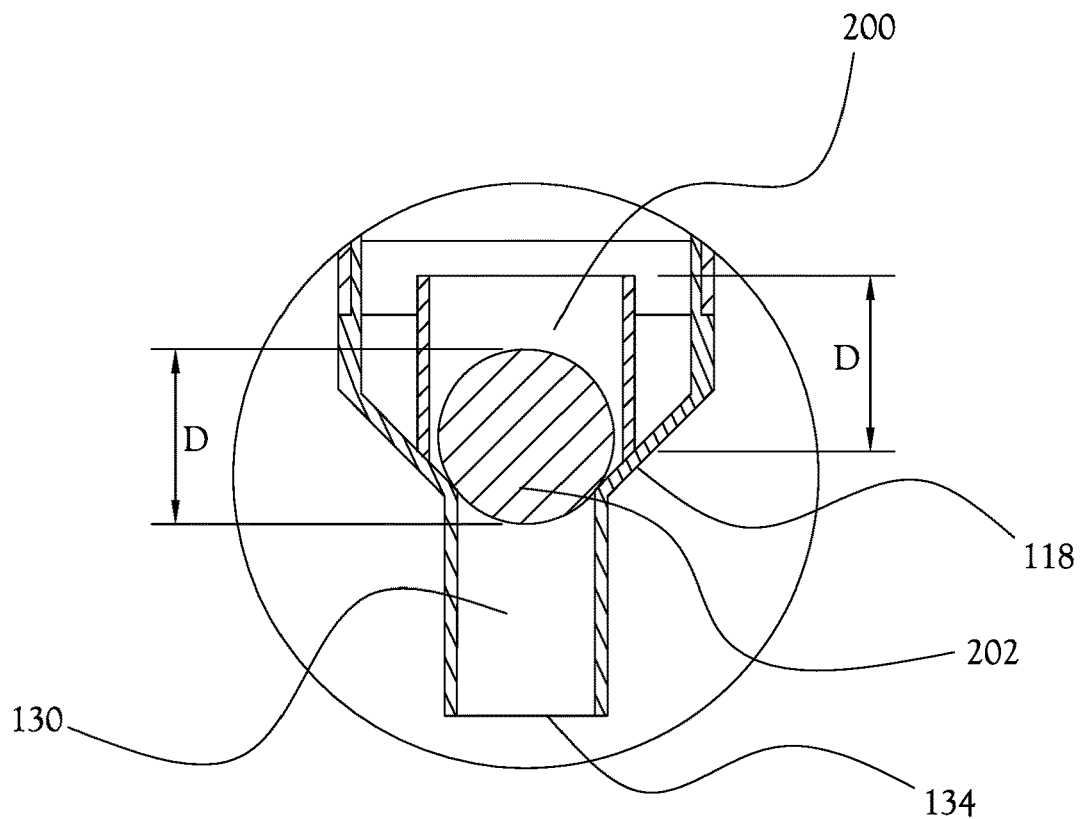
FIGS. 4A-B illustrate blown-up views of the bottom portion of the liquid sampling device according to two different example embodiments of the present general inventive concept.
Figure 4B:
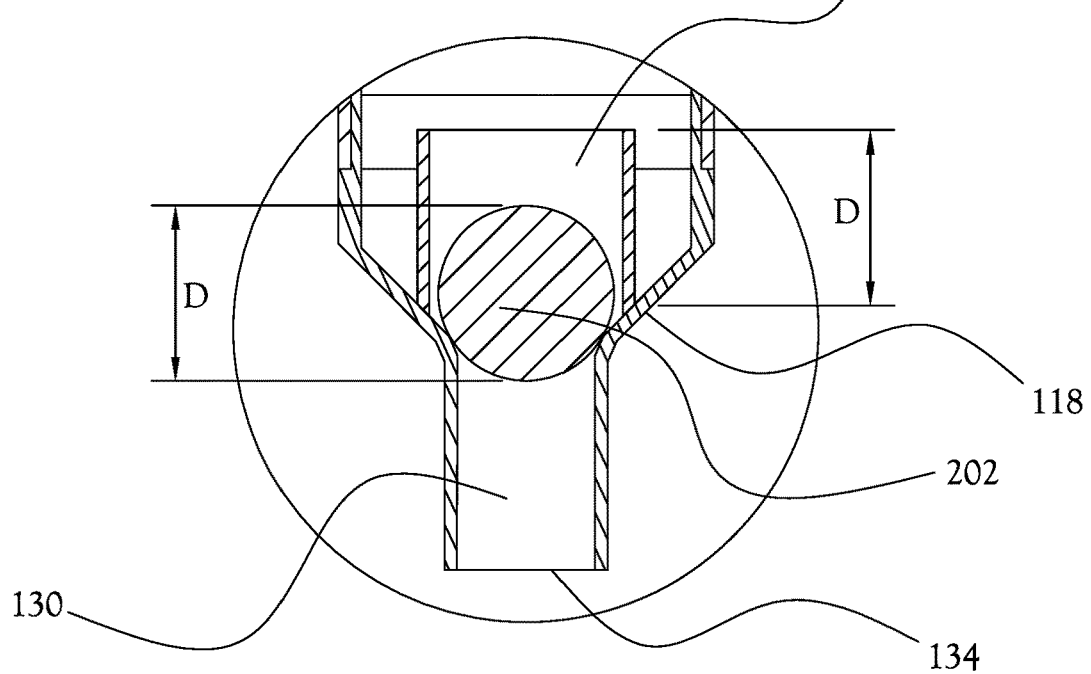

As previously described, the bottom cap 118 has an external annular flange 130 extending from the bottom cap 118 and sharing an axis with the cylindrical body 110, and an intake orifice 134 formed through the external annular flange 130 to allow liquid to flow into the liquid sampling device 100. A ball valve 202 is provided inside the liquid sampling device 100 to open and close the opening 134 in the bottom cap 118. The ball valve 202 is denser than water, but light enough to be displaced by water flowing upward through the external annular flange 130. Thus, the ball valve 202 has a density slight enough to float upward and allow liquid into the liquid sampling device 100 when the liquid sampling device 100 is lowered into the water in a testing well, but is sufficiently dense to sink and close the opening 134 due to the pressure of the sample in the liquid sampling device 100 when lifted out of the testing well. The bottom cap 118 of the example embodiment illustrated in FIG. 2A also includes an internal annular flange 200 that extends inwardly from an end of the bottom cap 118 and shares an axis with the cylindrical body 110. The internal annular flange 200 is formed with a diameter larger than the ball valve 202 such that the ball valve 202 can easily move inside the internal annular flange 200 to close the opening 134, but cannot fit between the internal annular flange 200 and the side of the cylindrical body 110 or bottom cap 118, depending upon the length of the internal annular flange 200. Such a configuration prevents the ball valve 202 from becoming unsettled and failing to work properly. For example, if a vortex is created during a draining of liquid from the bailer 100, the ball valve 202 could be manipulated by the vortex and prevented from properly closing the opening 134. The internal annular flange 200 can prevent such an occurrence by limiting the radial movement of the ball valve 202 when in proximity of the opening 134. In various example embodiments, the internal annular flange 200 may be formed such that an overall length of the internal annular flange 200 is substantially equal to the diameter of the ball valve 202 (such a configuration is illustrated in FIGS. 4A-B, described herein, in which "D" indicates the measure of the diameter of the ball valve). In other various example embodiments, the internal annular flange 200 may be formed such that an upper end of the internal annular flange 200 may be substantially even with an uppermost point of the ball valve 202 when the ball valve 202 is seated in the opening of the bottom cap 118. Various other example embodiments may include an internal annular flange 200 with other lengths. The internal annular flange 200 can also prevent at least a portion sediment or other such solids that may be present in the water sample from sinking downward in the collected water sample and interfering with the seal formed between the ball valve 202 and the opening in the bottom cap 118 formed by the external annular flange 130. Such sediment may collect in the area between the internal annular flange 200 and the inner surface of the bottom cap 118, rather than disrupting the operation of the ball valve 202.

In some embodiments, such as the embodiment illustrated in FIG. 2A, the liquid sampling device 100 optionally includes a weighted insert 206 configured to fit snugly inside the cylindrical body 110. The weighted insert 206 may be configured to stay in place in the cylindrical body 110 by way of an interference fit. The weighted insert 206 provides an anti-buoyancy to the liquid sampling device 100 so that the liquid sampling device may descend into the liquid in a testing well while maintaining a substantially vertical orientation. The weighted insert 206 may also be positioned such that the upward travel of the ball valve 202 is limited to the area beneath the weighted insert 206, so that a time taken for the ball valve 202 to close the opening 134 may be decreased. The weighted insert 206 may be provided with one or more openings through which the liquid may move into an area of the cylindrical body 110 above the weighted insert 206. In the example embodiment illustrated in FIG. 2A, the weighted insert 206 is provided with a central channel 210 to pass the liquid therethrough. A grating 212 is provided at a bottom of the central channel 210 to prevent the ball valve 202 from obstructing the central channel 210. The weighted insert 206 may also be provided with a plurality of recesses on a top portion thereof to allow an assembler to use a corresponding tool to move the weighted insert 206 to a desired location in the liquid sampling device 100. In various example embodiments, the weighted insert 206 may be provided with a plurality of notches formed at a circumference of the top of the weighted insert 206 to be employed in such tool manipulation. In various example embodiments, the fit of the weighted insert 206 inside the cylindrical body 110 is snug enough that the weighted member 206 cannot be moved without an externally applied force, such as by an assembler with a tool.

Those of skill in the art will recognize that various numbers and configurations of the above-discussed weighted inserts 206 may be used to accomplish the liquid sampling device 100 in accordance with various features of the present general inventive concept. For example, in various embodiments, a single weighted insert 206 is provided. In other embodiments, two or more weighted inserts 206 are provided. In still other embodiments, the overall weight and density of the liquid sampling device 100 is such that the liquid sampling device 100 achieves sufficient anti-buoyancy to allow the liquid sampling device 100 to descend into a liquid in a testing well at a desired rate, such that no weighted insert 206 need be provided.

Figure 3:
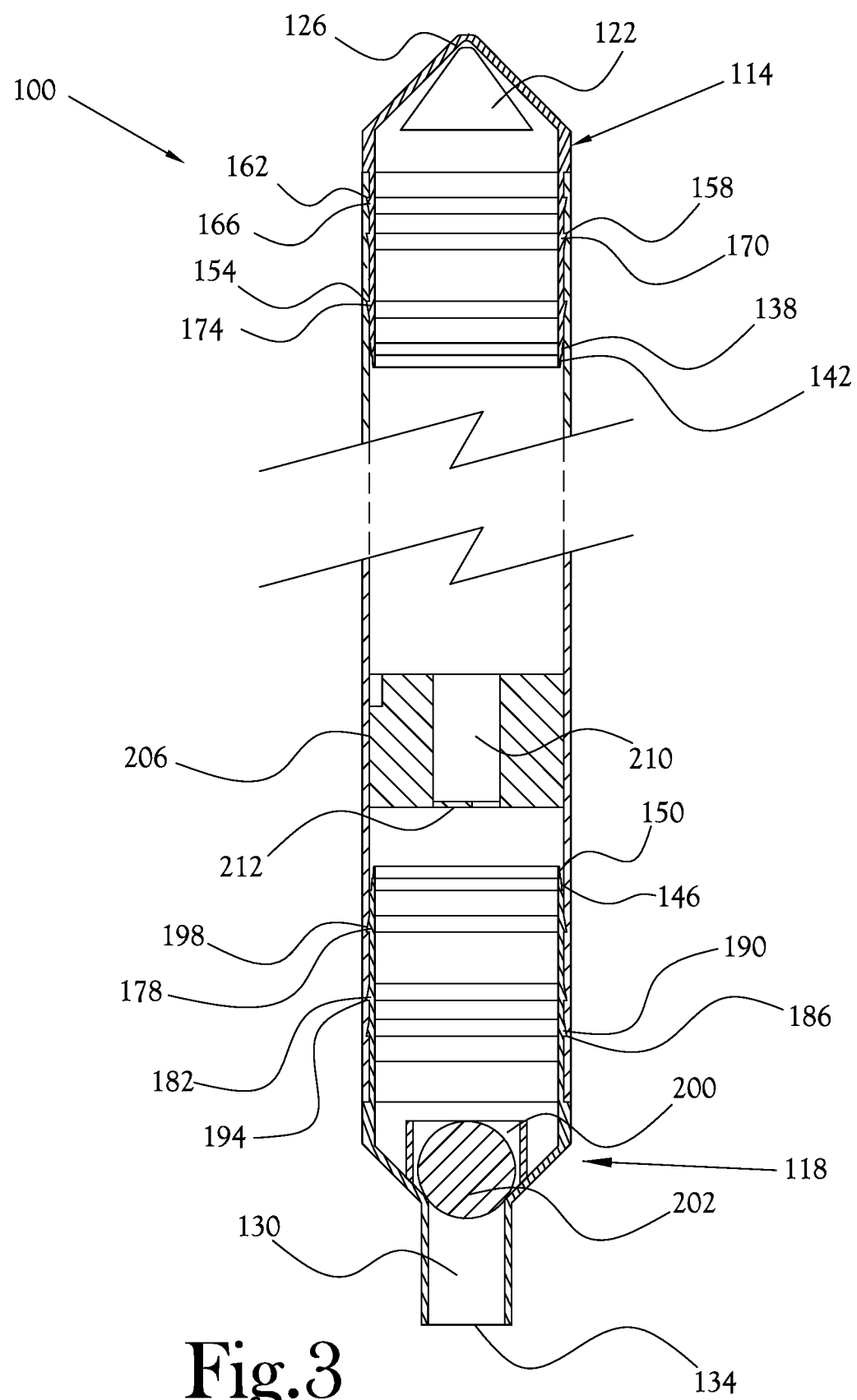
FIG. 3 illustrates an assembled cross section of the components illustrated in FIG. 2A.

FIG. 3 illustrates an assembled cross section of the components illustrated in FIG. 2A. As shown in FIG. 3, the previously described ridges and grooves are in register to form the plurality of snap fits that secure the caps 114,118 to the cylindrical body 110 of the bailer 100.

FIGS. 4A-B illustrate blown-up views of the bottom portion of the liquid sampling device according to two different example embodiments of the present general inventive concept. As previously described, an opening 134 is formed in the bottom cap 118 by the external annular flange 130, and the opening 134 may be closed when the ball valve 202 is seated in the opening 134 of the bottom cap 118. According to various example embodiments of the present general inventive concept, the portion of the assembly contacted by the ball valve 202 may be a sharp corner when transitioning from the interior of the bottom cap 118 to the interior of the external annular flange 130, as illustrated in FIG. 4A. According to various other example embodiments, the portion of the device transitioning from the interior of the bottom cap 118 to the interior of the external annular flange 130 may be beveled, as illustrated in FIG. 4B, and may therefore provide more possible contact surface for the ball valve 202. Such a configuration may be desirable, for example, when sediment or other bodies may be prone to collect near, or adhere to, the potential contact points between the ball valve 202 and the opening 134. Various other example embodiments may provide other types of structural configurations for the fitting of the ball valve 202 in the opening 134 of the bottom cap 118.

FIGS. 5A-B illustrate a drainage member for the liquid sampling device according to an example embodiment of the present general inventive concept. As previously described, when the bailer 100 is pulled out of a testing well with a sample contained therein, the weight of the contained liquid pushes down on the ball valve to close the opening 134 in the bottom cap 118 to prevent the liquid from escaping the bailer 100. Various example embodiments of the present general inventive concept include a selectably attachable drainage member 214, which is a hollow cylindrical body 218 formed to fit snuggle within the external annular flange 130 such that liquid may drain therethough without escaping between the drainage member 214 and the interior of the external annular flange 130, and such that the liquid may be drained neatly and carefully into a small receptacle. In order to push the ball valve 202 off of the opening 134, and to also prevent the ball valve 202 from preventing liquid from passing through the drainage member 214, the drainage member 214 may be formed with an angled end 222 on at least one end thereof to be inserted into the bailer 100. Since the inner diameter of the cylindrical body 218 of the drainage member 214 has to be smaller than the external annular flange 130 through which it is configured to snugly fit, and therefore could be blocked by the ball valve 202, the angled end 222 has an opening with more area than the diameter of the cylindrical body 218 itself, and one that cannot be blocked by the ball valve 202. In various example embodiments, the drainage member 214 may be provided with angled ends 222 at both ends thereof, to also prevent any such blockage from a receptacle into which the liquid is being drained from the bailer 100.

Various example embodiments of the present general inventive concept may provide a liquid sampling device including a substantially cylindrical body configured to have a first plurality of grooves formed concentrically and with irregular spacing proximate a first end of the cylindrical body, and a second plurality of grooves formed concentrically and with irregular spacing proximate a second end of the cylindrical body, a top cap having a substantially cylindrical insertion portion configured to fit inside the cylindrical body and to have a plurality of ridges formed concentrically thereon so as to correspond to the first plurality of grooves, and a cap portion formed with a suspension member configured to receive a suspension element from which the liquid sampling device may hang, and a bottom cap having a substantially cylindrical insertion portion configured to fit inside the cylindrical body and to have a plurality of ridges formed concentrically thereon so as to correspond to the second plurality of grooves, and a cap portion including an external annular flange forming an opening in the bottom cap to pass liquid therethrough into the liquid sampling device, wherein the ridges of the top and bottom caps are configured to form snap fits with the corresponding grooves of the cylindrical body. The ridges of the top and bottom caps may be angled on distal sides thereof, and flat on proximate sides thereof, and the grooves may have angled and flat sides substantially registering to the ridges of the top and bottom caps such that the flat sides of the corresponding ridges and grooves face one another when the snap fits are formed. According to various example embodiments of the present general inventive concept, the cylindrical body and the top and bottom caps may be formed of any of a variety of materials, such as for example polyethylene, polypropylene, polyvinyl chloride (PVC), or the like. The top and bottom caps may each be configured to have a plurality of step down portions at distal ends thereof to aid in guiding the insertion portions into the cylindrical body. The cap portion of the top cap may include a tapered portion with an opening formed to pass therethrough such that two symmetrical orifices are formed in the tapered portion, and a portion of the top cap may extend over the symmetrical orifices to form the suspension member. The bottom cap may include a tapered portion terminating at the external annular flange, and the external annular flange may be configured to share an axis with the cylindrical body. The bottom cap may include an internal annular flange configured to share an axis with the cylindrical body, the internal annular flange extending inwardly from the tapered portion of the bottom cap and having a larger diameter than the external annular flange, and the liquid sampling device further includes a ball valve configured to have a diameter larger than the external annular flange and smaller than the internal annular flange such that the ball valve may close the opening in the bottom cap formed by the external annular flange The internal annular flange may be configured to allow the ball valve to pass therethrough, and to prevent the ball valve from fitting between the internal annular flange and the cylindrical body or cylindrical insertion portion of the bottom cap. The internal annular flange may be configured to have a length that is equal to the diameter of the ball valve, or a length such that an upper end of the internal annular flange is substantially even with an uppermost point of the ball valve when the ball valve is seated in the opening of the bottom cap. The liquid sampling device may further include a weighted insert configured to fit snuggly inside the cylindrical body at a predetermined position to provide anti-buoyancy to the liquid sampling device and to limit upward movement of the ball valve while allowing liquid to pass therethrough. The weighted insert may be formed with a central channel configured to allow liquid therethrough and a grating provided at a bottom of the central channel configured to prevent the ball valve from blocking the central channel. The top and bottom caps may be hollow to form pathways from inside the cylindrical body to outside of the top and bottom caps. The liquid sampling device may further include a selectively attachable drainage member configured to be inserted through external annular flange to drain the liquid sampling device, the drainage member being formed so as to be hollow, to snugly fit inside the external annular flange, and having angled ends configured to prevent blockage of liquid flow therethrough. The grooves and ridges may be formed such that no more than one ridge of the top cap may be placed in any of the grooves of the cylindrical body until all of the ridges of the top cap are placed simultaneously in the corresponding grooves, and such that no more than one ridge of the bottom cap may be placed in any of the grooves of the cylindrical body until all of the ridges of the bottom cap are placed simultaneously in the corresponding grooves. The grooves and ridges may be configured such that an audible indicator of multiple ridges and grooves forming snap fits is louder than a single ridge and groove forming a snap fit.

Various example embodiments of the present general inventive concept may provide a liquid sampling device including a substantially cylindrical body having first and second ends, a top cap configured to cap a first end of the cylindrical body and formed with a suspension member configured to receive a suspension element from which the liquid sampling device may hang, a bottom cap configured to cap a second end of the cylindrical body and formed with an external annular flange forming an opening in the bottom cap and sharing an axis with the cylindrical body; a ball valve configured to have a diameter larger than the external annular flange such that the ball valve may close the opening in the bottom cap formed by the external annular flange, and a weighted insert configured to fit snuggly inside the cylindrical body at a predetermined position to provide anti-buoyancy to the liquid sampling device and to limit upward movement of the ball valve while allowing liquid to pass therethrough. The weighted insert may be formed with a central channel configured to allow liquid therethrough and a grating provided at a bottom of the central channel configured to prevent the ball valve from blocking the central channel. The weighted insert may be formed with a plurality of notches formed at a top portion thereof, the notches configured to provide a grip to be used in placement of the weighted insert in the cylindrical body. The notches may be formed symmetrically along a circumference of the top portion of the weighted insert. The bottom cap may include an internal annular flange extending inwardly from the bottom cap and having a larger diameter than the external annular flange, the internal annular flange being configured to share an axis with the cylindrical body, and the internal annular flange may be configured to allow the ball valve to pass therethrough, and to prevent the ball valve from fitting between the internal annular flange and the cylindrical body or the bottom cap.

Various example embodiments of the present general inventive concept may provide a liquid sampling device including a substantially cylindrical body configured to have a first plurality of grooves formed concentrically and with irregular spacing on an inner surface proximate a first end of the cylindrical body, and a second plurality of grooves formed concentrically and with irregular spacing on an inner surface proximate a second end of the cylindrical body, a top cap having a substantially cylindrical insertion portion configured to fit snugly inside the cylindrical body and to have a plurality of step down portions at a distal end thereof, the insertion portion of the top cap configured to have a plurality of ridges formed concentrically thereon so as to correspond to the first plurality of grooves, and a cap portion configured to abut against the first end of the cylindrical body and to have a tapered portion with an opening formed to pass therethrough such that two symmetrical orifices are formed in the tapered portion, a bottom cap having a substantially cylindrical insertion portion configured to fit snugly inside the cylindrical body and to have a plurality of step down portions at a distal end thereof, the insertion portion of the bottom cap configured to have a plurality of ridges formed concentrically thereon so as to correspond to the second plurality of grooves, and a cap portion configured to abut against the second end of the cylindrical body, to have a tapered portion terminating at an external annular flange forming an opening in the bottom cap, and to have an internal annular flange extending inwardly from the tapered portion and having a larger diameter than the external annular flange, a ball valve configured to have a diameter larger than the external annular flange and smaller than the internal annular flange such that the ball valve may close the opening in the bottom cap formed by the external annular flange, and a weighted insert configured to fit snuggly inside the cylindrical body at a predetermined position to provide anti-buoyancy to the liquid sampling device and to limit upward movement of the ball valve, the weighted insert having a central channel configured to allow liquid therethrough and a grating provided at a bottom of the central channel configured to prevent the ball valve from blocking the central channel, wherein the top and bottom caps are hollow to form pathways from inside the cylindrical body to outside of the top and bottom caps, and wherein the ridges of the top and bottom caps are configured to form snap fits with the corresponding grooves of the cylindrical body.

Numerous variations, modifications, and additional embodiments are possible, and accordingly, all such variations, modifications, and embodiments are to be regarded as being within the spirit and scope of the present general inventive concept. For example, regardless of the content of any portion of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated.

It is noted that the simplified diagrams and drawings included in the present application do not illustrate all the various connections and assemblies of the various components, however, those skilled in the art will understand how to implement such connections and assemblies, based on the illustrated components, figures, and descriptions provided herein, using sound engineering judgment. Numerous variations, modification, and additional embodiments are possible, and, accordingly, all such variations, modifications, and embodiments are to be regarded as being within the spirit and scope of the present general inventive concept.

While the present general inventive concept has been illustrated by description of several example embodiments, and while the illustrative embodiments have been described in detail, it is not the intention of the applicant to restrict or in any way limit the scope of the general inventive concept to such descriptions and illustrations. Instead, the descriptions, drawings, and claims herein are to be regarded as illustrative in nature, and not as restrictive, and additional embodiments will readily appear to those skilled in the art upon reading the above description and drawings. Additional modifications will readily appear to those skilled in the art. Accordingly, departures may be made from such details without departing from the spirit or scope of applicant's general inventive concept.

The invention claimed is:

1. A liquid sampling device, comprising:
a substantially cylindrical body configured to have a first plurality of grooves formed concentrically and with irregular spacing proximate a first end of the cylindrical body, and a second plurality of grooves formed concentrically and with irregular spacing proximate a second end of the cylindrical body;
a top cap having a substantially cylindrical insertion portion configured to fit inside the cylindrical body and to have a plurality of ridges formed concentrically thereon so as to correspond to the first plurality of grooves, and a cap portion formed with a suspension member configured to receive a suspension element from which the liquid sampling device may hang; and
a bottom cap having a substantially cylindrical insertion portion configured to fit inside the cylindrical body and to have a plurality of ridges formed concentrically thereon so as to correspond to the second plurality of grooves, and a cap portion including an external annular flange forming an opening in the bottom cap to pass liquid therethrough into the liquid sampling device;
wherein the ridges of the top and bottom caps are configured to form snap fits with the corresponding grooves of the cylindrical body.

2. The liquid sampling device of claim 1, wherein the ridges of the top and bottom caps are angled on distal sides thereof, and flat on proximate sides thereof; and
wherein the grooves have angled and flat sides substantially register to the ridges of the top and bottom caps such that the flat sides of the corresponding ridges and grooves face one another when the snap fits are formed.

3. The liquid sampling device of claim 1, wherein the top and bottom caps are formed of polyethylene, and the cylindrical body is formed of polyvinyl chloride (PVC) or polyethylene.

4. The liquid sampling device of claim 1, wherein the top and bottom caps are each configured to have a plurality of step down portions at distal ends thereof to aid in guiding the insertion portions into the cylindrical body.

5. The liquid sampling device of claim 1, wherein the cap portion of the top cap includes a tapered portion with an opening formed to pass therethrough such that two symmetrical orifices are formed in the tapered portion; and wherein a portion of the top cap extending over the symmetrical orifices forms the suspension member.

6. The liquid sampling device of claim 1, wherein the bottom cap includes a tapered portion terminating at the external annular flange; and
wherein the external annular flange is configured to share an axis with the cylindrical body.

7. The liquid sampling device of claim 6, wherein the bottom cap includes an internal annular flange configured to share an axis with the cylindrical body, the internal annular flange extending inwardly from the tapered portion of the bottom cap and having a larger diameter than the external annular flange; and
wherein the liquid sampling device further comprises a ball valve configured to have a diameter larger than the external annular flange and smaller than the internal annular flange such that the ball valve may close the opening in the bottom cap formed by the external annular flange.

8. The liquid sampling device of claim 7, wherein the internal annular flange is configured to allow the ball valve to pass therethrough, and to prevent the ball valve from fitting between the internal annular flange and the cylindrical body or cylindrical insertion portion of the bottom cap.

9. The liquid sampling device of claim 8, further comprising a weighted insert configured to fit snugly inside the cylindrical body at a predetermined position to provide anti-buoyancy to the liquid sampling device and to limit upward movement of the ball valve while allowing liquid to pass therethrough.

10. The liquid sampling device of claim 9, wherein the weighted insert is formed with a central channel configured to allow liquid therethrough and a grating provided at a bottom of the central channel configured to prevent the ball valve from blocking the central channel.

11. The liquid sampling device of claim 7, wherein the internal annular flange is configured to have a length that is equal to the diameter of the ball valve, or a length such that an upper end of the internal annular flange is substantially even with an uppermost point of the ball valve when the ball valve is seated in the opening of the bottom cap.

12. The liquid sampling device of claim 1, further comprising a selectively attachable drainage member configured to be inserted through external annular flange to drain the liquid sampling device, the drainage member being formed so as to be hollow, to snugly fit inside the external annular flange, and having angled ends configured to prevent blockage of liquid flow therethrough.

13. The liquid sampling device of claim 1, wherein the grooves and ridges are formed such that no more than one ridge of the top cap may be placed in any of the grooves of the cylindrical body until all of the ridges of the top cap are placed simultaneously in the corresponding grooves, and such that no more than one ridge of the bottom cap may be placed in any of the grooves of the cylindrical body until all of the ridges of the bottom cap are placed simultaneously in the corresponding grooves.

14. The liquid sampling device of claim 13, wherein the grooves and ridges are configured such that an audible indicator of multiple ridges and grooves forming snap fits is louder than a single ridge and groove forming a snap fit.

15. A liquid sampling device, comprising:
a substantially cylindrical body configured to have a first plurality of grooves formed concentrically and with irregular spacing on an inner surface proximate a first end of the cylindrical body, and a second plurality of grooves formed concentrically and with irregular spacing on an inner surface proximate a second end of the cylindrical body;
a top cap having a substantially cylindrical insertion portion configured to fit snugly inside the cylindrical body and to have a plurality of step down portions at a distal end thereof, the insertion portion of the top cap configured to have a plurality of ridges formed concentrically thereon so as to correspond to the first plurality of grooves, and a cap portion configured to abut against the first end of the cylindrical body and to have a tapered portion with an opening formed to pass therethrough such that two symmetrical orifices are formed in the tapered portion;
a bottom cap having a substantially cylindrical insertion portion configured to fit snugly inside the cylindrical body and to have a plurality of step down portions at a distal end thereof, the insertion portion of the bottom cap configured to have a plurality of ridges formed concentrically thereon so as to correspond to the second plurality of grooves, and a cap portion configured to abut against the second end of the cylindrical body, to have a tapered portion terminating at an external annular flange forming an opening in the bottom cap, and to have an internal annular flange extending inwardly from the tapered portion and having a larger diameter than the external annular flange;
a ball valve configured to have a diameter larger than the external annular flange and smaller than the internal annular flange such that the ball valve may close the opening in the bottom cap formed by the external annular flange; and
a weighted insert configured to fit snugly inside the cylindrical body at a predetermined position to provide anti-buoyancy to the liquid sampling device and to limit upward movement of the ball valve, the weighted insert having a central channel configured to allow liquid therethrough and a grating provided at a bottom of the central channel configured to prevent the ball valve from blocking the central channel;
wherein the top and bottom caps are hollow to form pathways from inside the cylindrical body to outside of the top and bottom caps; and
wherein the ridges of the top and bottom caps are configured to form snap fits with the corresponding grooves of the cylindrical body.

* * * * *